(12) United States Patent
Hosaka et al.

(10) Patent No.: US 9,173,699 B2
(45) Date of Patent: Nov. 3, 2015

(54) ENDOSCOPIC FORCEPS

(75) Inventors: Makoto Hosaka, Ritto (JP); Kazuo Abe, Ritto (JP); Eiichi Uemura, Ritto (JP)

(73) Assignee: YAMASHINA SEIKI CO., LTD., Ritto-shi (JP)

( * ) Notice: Subject to any disclaimer, the term of this patent is extended or adjusted under 35 U.S.C. 154(b) by 175 days.

(21) Appl. No.: 14/127,402

(22) PCT Filed: May 22, 2012

(86) PCT No.: PCT/JP2012/062994
§ 371 (c)(1),
(2), (4) Date: Dec. 18, 2013

(87) PCT Pub. No.: WO2013/005485
PCT Pub. Date: Jan. 10, 2013

(65) Prior Publication Data
US 2014/0135756 A1    May 15, 2014

(30) Foreign Application Priority Data

Jul. 7, 2011   (JP) .................................. 2011-151308

(51) Int. Cl.
| *A61B 18/18* | (2006.01) |
| *A61B 18/14* | (2006.01) |
| *A61B 18/00* | (2006.01) |
| *A61B 17/29* | (2006.01) |

(52) U.S. Cl.
CPC ......... *A61B 18/1447* (2013.01); *A61B 18/1445* (2013.01); *A61B 18/1815* (2013.01);
(Continued)

(58) Field of Classification Search
CPC ........... A61B 18/1442; A61B 18/1445; A61B 18/1447; A61B 2018/145; A61B 2018/1452; A61B 2018/1455; A61B 2018/1457
See application file for complete search history.

(56) References Cited

U.S. PATENT DOCUMENTS

2007/0282331 A1   12/2007   Kawano

FOREIGN PATENT DOCUMENTS

| JP | 8-509623 A   | 10/1996 |
| JP | 2003-299670 A | 10/2003 |

(Continued)

OTHER PUBLICATIONS

International Search Report dated Aug. 28, 2012 issued in corresponding application No. PCT/JP2012/062994.
(Continued)

*Primary Examiner* — Michael Peffley
*Assistant Examiner* — Daniel Fowler
(74) *Attorney, Agent, or Firm* — Westerman, Hattori, Daniels & Adrian, LLP

(57) ABSTRACT

An endoscopic forceps is provided. A movable blade electrode and a fixed blade electrode form a pair of electrodes. The fixed blade electrode is electrically contacted onto an external electric conductor of a coaxial cable in the sheath conduit. A force application point of the movable blade electrode is connected to a center electric conductor of the coaxial cable. A pivot point of the movable blade electrode is provided on the movable blade electrode. The coaxial cable is slid with respect to the sheath conduit so that parallel moving added to the coaxial cable is transmitted to the movable blade electrode as turnable moving about the pivot point via the force application point of the movable blade electrode. A high frequency wave can be applied between the movable blade electrode and the fixed blade electrode via the external electric conductor and the center electric conductor of the coaxial cable.

4 Claims, 2 Drawing Sheets

(52) U.S. Cl.
CPC . *A61B2017/2902* (2013.01); *A61B 2018/0063* (2013.01); *A61B 2018/00589* (2013.01); *A61B 2018/00601* (2013.01); *A61B 2018/00982* (2013.01); *A61B 2018/1415* (2013.01)

(56) References Cited

FOREIGN PATENT DOCUMENTS

| | | |
|---|---|---|
| JP | 2006-518258 A | 8/2006 |
| JP | 2007-229294 A | 9/2007 |
| JP | 2007-282666 A | 11/2007 |
| JP | 2007-319679 A | 12/2007 |
| JP | 2009-119087 A | 6/2009 |
| JP | 2009-142513 A | 7/2009 |
| WO | 94/17741 A1 | 8/1994 |

OTHER PUBLICATIONS

Translation of the International Preliminary Report on Patentability dated Jan. 16, 2014 of PCT/JP2012/062994, forms PCT/IB/338, PCT/IB/337 and PCT/ISA/237 (6 pages).

ENDOSCOPIC FORCEPS

TECHNICAL FIELD

The present invention relates to an endoscopic forceps.

BACKGROUND ART

Conventionally, as an endoscopic forceps, there has been known a medical treatment instrument including a first turnable electrode, and a second fixed electrode opposite to the first electrode, wherein a turning axis of the first electrode is provided outward of a center axis between the first electrode and the second electrode, the first electrode is turned about the turning axis so that a biological tissue is sandwiched between the first electrode and the second electrode, the first electrode and the second electrode are opposite to each other in parallel so that a microwave is supplied to the first electrode and the second electrode to coagulate the biological tissue, and the first electrode is turned about the turning axis to be brought into contact with the second electrode from the end thereof so that the biological tissue is sheared (Patent document 1).

PRIOR ART DOCUMENTS

Patent Documents

Patent document 1: JP-A-2007-282666

SUMMARY OF THE INVENTION

Problems to be Solved by the Invention

However, the conventional medical treatment instrument has a complicated configuration so that the number of components is large. Consequently, it is difficult to apply the conventional medical treatment instrument to an endoscopic forceps.

That is, an object of the present invention is to provide a forceps which has a non-complicated configuration and can be reduced in diameter to be applicable to an endoscopic forceps.

Solutions to the Problems

An endoscopic forceps of the present invention is an endoscopic forceps in which a movable blade electrode and a fixed blade electrode form a pair of electrodes, wherein the fixed blade electrode fixed to a sheath conduit is arranged to be electrically contacted onto an external electric conductor of a coaxial cable in the sheath conduit, wherein a force application point of the movable blade electrode is connected to a center electric conductor of the coaxial cable, wherein a pivot point of the movable blade electrode is provided on the movable blade electrode which is turnably connected to an electric insulator fixed to the fixed blade electrode or the sheath conduit, or is provided on the electric insulator fixed to the movable blade electrode which is turnably connected to the sheath conduit or the fixed blade electrode, wherein the coaxial cable is slid with respect to the sheath conduit so that parallel moving added to the coaxial cable is transmitted to the movable blade electrode as turnable moving about the pivot point via the force application point of the movable blade electrode to open and close the movable blade electrode and the fixed blade electrode, wherein a high frequency wave can be applied between the movable blade electrode and the fixed blade electrode via the external electric conductor and the center electric conductor of the coaxial cable.

The fixed blade electrode is fixed to the sheath conduit to form the pair of electrodes together with the movable blade electrode. Both the fixed blade electrode and the movable blade electrode which function as electrodes may be made of metals or ceramics, and may be surface protected (metal plated or coated with a fluororesin and the like).

The sheath conduit inserts the coaxial cable thereinto so that the coaxial cable can be slid with respect to the sheath conduit. That is, the sheath conduit guides the movable blade electrode and the fixed blade electrode to an affected part to push and pull the coaxial cable in the sheath conduit. In addition, the sheath conduit may be flexible or rigid, one portion thereof may be flexible, and the other portion thereof may be rigid. Further, the sheath conduit may be an electric insulator or an electric conductor, but is preferably the electric insulator in view of handling.

The cross section of the sheath conduit perpendicular to the center axis thereof is preferably circular. That is, the sheath conduit is preferably a circular cylindrical tube.

The maximum length of the cross section of the sheath conduit perpendicular to the center axis thereof is preferably 2 mm to 4 mm, more preferably, 2.5 mm to 3.5 mm. When the sheath conduit is a circular cylindrical tube, the diameter of the cross section of the sheath conduit perpendicular to the center axis thereof is preferably 2 mm to 4 mm, more preferably, 2.5 mm to 3.5 mm.

The fixed blade electrode is contacted onto the external electric conductor of the coaxial cable in the sheath conduit so that the fixed blade electrode and the external electric conductor of the coaxial cable maintain electric contact by sliding the coaxial cable.

The force application point of the movable blade electrode is connected to the center electric conductor of the coaxial cable so that moving by sliding the coaxial cable with respect to the sheath conduit is transmitted to the force application point. The center electric conductor of the coaxial cable and the movable blade electrode are electrically connected.

The pivot point of the movable blade electrode is provided on the movable blade electrode which is turnably connected to the electric insulator fixed to the fixed blade electrode or the sheath conduit, or the pivot point of the movable blade electrode is provided on the electric insulator fixed to the movable blade electrode which is turnably connected to the sheath conduit or the fixed blade electrode.

Examples of the electric insulator include engineering plastics {polyetheretherketone (PEEK), polyethersulfone (PES), polyamide (PA), polyamide imide (PAI), polyimide (PI), polyphenylene sulfide (PPS), polybenzimidazole (PBI) and the like}, fluororesins {polytetrafluoroethylene, polychlorotrifluoroethylene, polyvinylidene fluoride, polyvinyl fluoride, a perfluoroalkoxy fluororesin, a tetrafluoroethylene-hexafluoropropylene copolymer, an ethylene-tetrafluoroethylene copolymer, an ethylene-chlorotrifluoroethylene copolymer and the like}, and ceramics {alumina ($Al_2O_3$), zirconia ($ZrO_2$), silicon carbide (SiC), silicon nitride ($Si_3N_4$) and the like}.

In the endoscopic forceps of the present invention, the coaxial cable is slid with respect to the sheath conduit so that parallel moving (or pushing and pulling) added to the coaxial cable can be transmitted to the movable blade electrode as turnable moving about the pivot point via the force application point of the movable blade electrode to open and close the movable blade electrode and the fixed blade electrode. As in the known forceps, a handle is opened and closed so that the coaxial cable can be slid with respect to the sheath conduit to add parallel moving (or pushing and pulling) to the coaxial cable.

In the endoscopic forceps, the high frequency wave can be applied between the movable blade electrode and the fixed blade electrode via the external electric conductor and the center electric conductor of the coaxial cable. By applying the high frequency wave, a biological tissue between the movable blade electrode and the fixed blade electrode can be heated. Stop of bleeding, cutting, coagulation and the like can thus be achieved.

Preferably, the high frequency wave is an electric wave having a frequency of approximately 300 KHz to 100 GHz. More preferably, the high frequency wave is a microwave (an electric wave having a frequency of 13 MHz to 25 GHz). Particularly preferably, the high frequency wave is a microwave having a frequency of 900 MHz to 6 GHz. Most preferably, the high frequency wave is a microwave having a frequency of 2.45 GHz.

An endoscopic forceps apparatus of the present invention includes the endoscopic forceps, and a high frequency wave transmitter.

The endoscopic forceps and the high frequency wave transmitter are connected by the coaxial cable so that the high frequency wave generated by the high frequency wave transmitter is transmitted to the movable blade electrode and the fixed blade electrode via the coaxial cable.

The high frequency wave transmitter is not limited as long as it can transmit the above frequencies, and its output is preferably approximately 10 W to 200 W.

Advantages of the Invention

In the endoscopic forceps of the present invention, the coaxial cable (including the center electric conductor, the electric insulator, the external electric conductor, and the protective sheath) can apply the high frequency wave to the movable blade electrode and the fixed blade electrode, and can transmit turnable moving to the movable blade electrode. Therefore, the endoscopic forceps can reduce the number of components to have a simple configuration.

The conventional medical treatment instrument has a complicated configuration so that the number of components is large. Consequently, it is difficult to apply the conventional medical treatment instrument to an endoscopic forceps. The endoscopic forceps of the present invention can be reduced in diameter to be applicable to an endoscopic operation and a celioscopic operation. The endoscopic forceps of the present invention is also applicable to a typical direct vision operation (surgical operation, brain surgery, otological surgery and the like).

The endoscopic forceps of the present invention is a forceps having at least one of a gripping function, a shearing blade function, and a coagulation function, and enables closing, stop of bleeding, cutting and coagulation of a duct tissue (a blood vessel, a bile duct and the like), stop of bleeding, cutting, coagulation of a cancer tissue and so on, and the like. In addition, the endoscopic forceps of the present invention is applicable to cutting of an operation tool (suture thread and the like).

The endoscopic forceps apparatus of the present invention includes the endoscopic forceps, and the high frequency wave transmitter. Therefore, the endoscopic forceps apparatus of the present invention can reduce the number of components to have a simple configuration.

The endoscopic forceps apparatus of the present invention is applicable to an endoscopic operation and a celioscopic operation. The endoscopic forceps apparatus of the present invention is also applicable to a typical direct vision operation (surgical operation, brain surgery, otological surgery and the like).

MODE FOR CARRYING OUT THE INVENTION

Hereinafter, an endoscopic forceps of the present invention will be described in more detail with reference to the drawings. Unless otherwise specified, the first described matter is sharably applicable to the description of the drawings thereafter.

Figure 1:
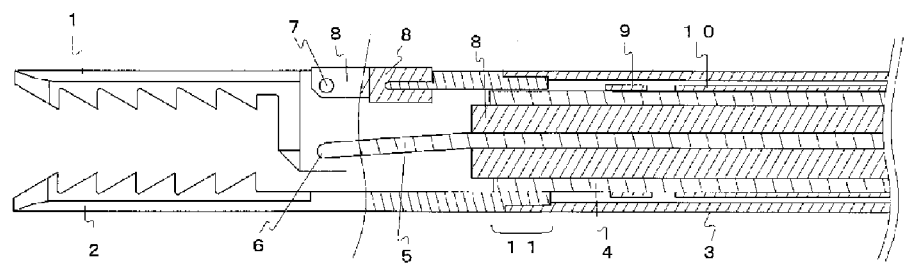
FIG. 1 is a partially side view which conceptually shows an embodiment of an endoscopic forceps of the present invention {in an example in which a movable blade electrode and a fixed blade electrode are of the gripping type, an example in which a pivot point of the movable blade electrode is provided on the movable blade electrode} (the right half is a partially cross-sectional view).
Figure 2:
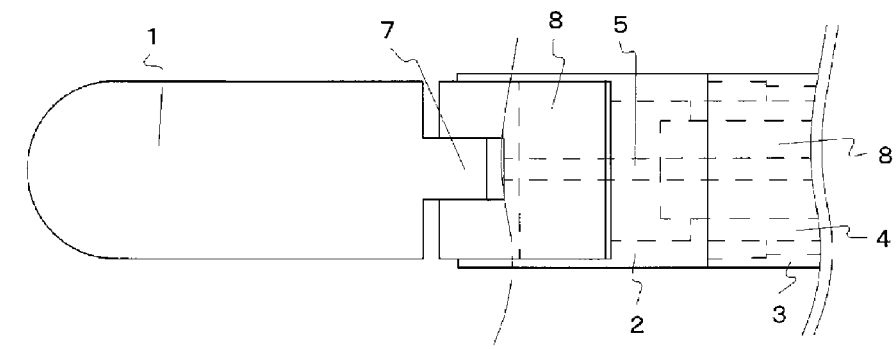
FIG. 2 is a partial plan view which conceptually shows an embodiment of the endoscopic forceps of the present invention {an example in which the movable blade electrode and the fixed blade electrode are of the gripping type} (the right half is a partially perspective plan view).

<FIGS. 1 and 2>

FIG. 1 is a partially side view which conceptually shows an embodiment of an endoscopic forceps of the present invention {in an example in which a movable blade electrode and a fixed blade electrode are of the gripping type, an example in which a pivot point of the movable blade electrode is provided on the movable blade electrode} (the right half is a partially cross-sectional view). FIG. 2 is a partial plan view which conceptually shows an embodiment of the endoscopic forceps {an example in which the movable blade electrode and the fixed blade electrode are of the gripping type} (the right half is a partially perspective plan view).

In the endoscopic forceps shown in FIGS. 1 and 2, the ends of a movable blade electrode (1) and a fixed blade electrode (2) are of the gripping type. In FIGS. 1 and 2, the ends of the gripping type form a crocodile mouth shape. However, the ends of the movable blade electrode (1) and the fixed blade electrode (2) are not limited to the crocodile mouth shape, and may have the same shape as a claw forceps, a retraction gripping forceps, a supporting hook forceps, a babcock forceps, a Debakey forceps and a lymph node gripping forceps and a similar shape thereto and the like.

The fixed blade electrode (2) includes the end (in crocodile mouth shape), and a cylindrical base. Part of a sheath conduit (3) (circular cylindrical tube) covers part of the base, so that both are connected and fixed to each other.

The fixed blade electrode (2) is contacted onto an external electric conductor (4) of a coaxial cable in the sheath conduit (3) by a slidable electric contacting portion (11) so that the fixed blade electrode (2) and the external electric conductor (4) of the coaxial cable maintain electric contact by sliding the coaxial cable.

A force application point (6) of the movable blade electrode (1) is connected to a center electric conductor (5) of the coaxial cable so that moving by sliding the coaxial cable with respect to the sheath conduit (3) is transmitted to the force application point (6). The center electric conductor (5) of the coaxial cable and the movable blade electrode (1) are electrically connected.

A pivot point (7) of the movable blade electrode (1) is provided on the movable blade electrode (1) which is turnably connected to an electric insulator (8) fixed to the base of the fixed blade electrode (2).

Figure 3:
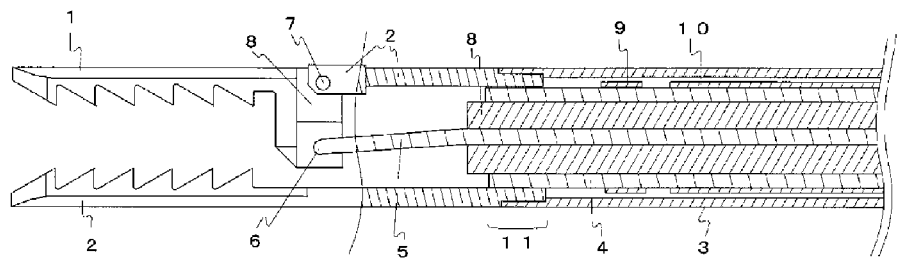
FIG. 3 is a partially side view which conceptually shows an embodiment of an endoscopic forceps of the present invention {in an example in which a movable blade electrode and a fixed blade electrode are of the gripping type, an example in which a pivot point of the movable blade electrode is provided on an electric insulator fixed to the movable blade electrode} (the right half is a partially cross-sectional view).

The pivot point (7) of the movable blade electrode (1) may be provided on the movable blade electrode (1) which is turnably connected to the sheath conduit (3). Alternatively, the pivot point (7) of the movable blade electrode (1) may be provided on the electric insulator (8) fixed to the movable blade electrode (1) which is turnably connected to the sheath conduit (3) or the fixed blade electrode (2) (see FIG. 3).

In the endoscopic forceps of the present invention, the coaxial cable is slid with respect to the sheath conduit (3) so that parallel moving (or pushing and pulling) added to the coaxial cable can be transmitted to the movable blade electrode (1) as turnable moving about the pivot point (7) via the force application point (6) of the movable blade electrode (1) to open and close the movable blade electrode (1) and the fixed blade electrode (2). A stopper (9) may be provided on the coaxial cable to limit the slidable (parallel moving) range. In FIG. 1, the stopper (9) is provided around the external electric conductor (4) to come into collision with the base of the fixed blade electrode (2) for limiting sliding (parallel moving).

In addition to the function as a forceps, as in the conventional forceps, in the endoscopic forceps of the present invention, the high frequency wave is applied between the movable blade electrode (1) and the fixed blade electrode (2) via the external electric conductor (4) and the center electric conductor (5) of the coaxial cable so that a biological tissue and the like between the movable blade electrode (1) and the fixed blade electrode (2) can be heated. Stop of bleeding, cutting, coagulation and the like can be achieved.

Figure 4:
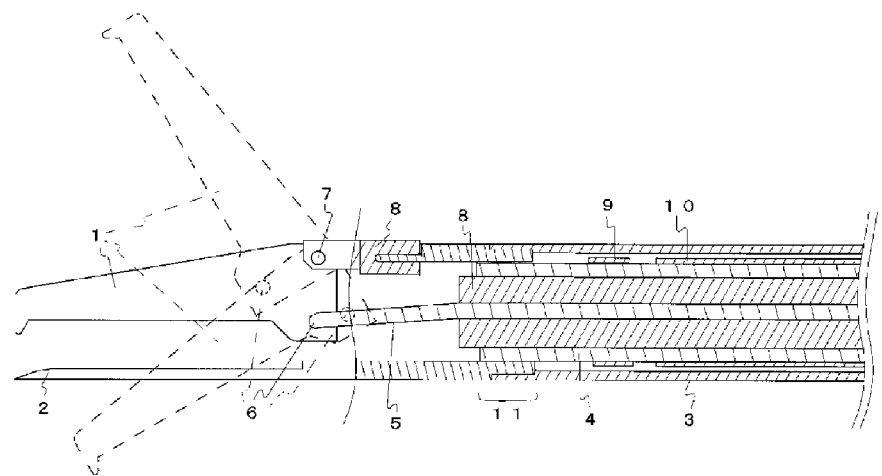
FIG. 4 is a partially side view which conceptually shows an embodiment of an endoscopic forceps of the present invention {an example in which a movable blade electrode and a fixed blade electrode are of the shearing blade type} (the right half is a partially cross-sectional view).
Figure 5:
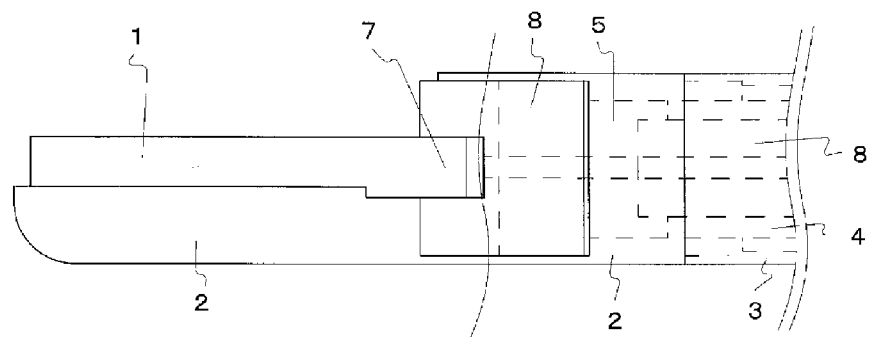
FIG. 5 is a partial plan view which conceptually shows an embodiment of the endoscopic forceps of the present invention {an example in which the movable blade electrode and the fixed blade electrode are of the shearing blade type} (the right half is a partially perspective plan view).

<FIGS. 4 and 5>

FIG. 4 is a partially side view which conceptually shows an embodiment of an endoscopic forceps of the present invention {an example in which a movable blade electrode and a fixed blade electrode are of the shearing blade type} (the right half is a partially cross-sectional view). FIG. 5 is a partial plan view which conceptually shows an embodiment of the endoscopic forceps {an example in which the movable blade electrode and the fixed blade electrode are of the shearing blade type} (the right half is a partially perspective plan view).

In the endoscopic forceps shown in FIGS. 4 and 5, the ends of a movable blade electrode (1) and a fixed blade electrode (2) are of the shearing blade type. The ends of the movable blade electrode (1) and the fixed blade electrode (2) are not limited to the shearing blade type shown in FIGS. 4 and 5, and can be changed according to application, as needed.

The fixed blade electrode (2) includes the end, and a cylindrical base. Part of a sheath conduit (3) (circular cylindrical tube) covers part of the base, so that both are connected and fixed to each other.

The fixed blade electrode (2) is contacted onto an external electric conductor (4) of a coaxial cable in the sheath conduit (3) by a slidable electric contacting portion (11) so that the fixed blade electrode (2) and the external electric conductor (4) of the coaxial cable maintain electric contact by sliding the coaxial cable.

A force application point (6) of the movable blade electrode (1) is connected to a center electric conductor (5) of the coaxial cable so that a moving energy by sliding the coaxial cable with respect to the sheath conduit (3) is transmitted to the force application point (6). The center electric conductor (5) of the coaxial cable and the movable blade electrode (1) are electrically connected.

A pivot point (7) of the movable blade electrode (1) is provided on the movable blade electrode (1) which is turnably connected to an electric insulator (8) fixed to the base of the fixed blade electrode (2).

The pivot point (7) of the movable blade electrode (1) may be provided on the movable blade electrode (1) which is turnably connected to the sheath conduit (3). Alternatively, the pivot point (7) of the movable blade electrode (1) may be provided on the electric insulator (8) fixed to the movable blade electrode (1) which is turnably connected to the sheath conduit (3) or the fixed blade electrode (2).

In the endoscopic forceps of the present invention, the coaxial cable is slid with respect to the sheath conduit (3) so that parallel moving (or pushing and pulling) added to the coaxial cable can be transmitted to the movable blade electrode (1) as turnable moving about the pivot point (7) via the force application point (6) of the movable blade electrode (1) to open and close the movable blade electrode (1) and the fixed blade electrode (2). A stopper (9) may be provided on the coaxial cable to limit the slidable (parallel moving) range. In FIG. 4, the stopper (9) is provided around the external electric conductor (4) to come into collision with the base of the fixed blade electrode (2) for limiting sliding (parallel moving).

In addition to the function as a forceps, as in the conventional forceps, in the endoscopic forceps of the present invention, the high frequency wave is applied between the movable blade electrode (1) and the fixed blade electrode (2) via the external electric conductor (4) and the center electric conductor (5) of the coaxial cable so that a biological tissue and the like between the movable blade electrode (1) and the fixed blade electrode (2) can be heated. Stop of bleeding, cutting, coagulation and the like can thus be achieved.

DESCRIPTION OF REFERENCE SIGNS

1 Movable blade electrode
2 Fixed blade electrode
3 Sheath conduit
4 External electric conductor
5 Center electric conductor
6 A force application point of a movable blade electrode
7 A pivot point of a movable blade electrode
8 Electric insulator
9 Stopper
10 Protected sheath of a coaxial cable
11 Slidable electric contacting portion

The invention claimed is:

1. An endoscopic forceps in which a movable blade electrode and a fixed blade electrode form a pair of electrodes, wherein the fixed blade electrode fixed to a sheath conduit is arranged to be electrically contacted onto an external electric conductor of a coaxial cable in the sheath conduit, wherein a force application point of the movable blade electrode is connected to a center electric conductor of the coaxial cable, wherein a pivot point of the movable blade electrode is provided on the movable blade electrode which is turnably connected to an electric insulator fixed to the fixed blade electrode or the sheath conduit, or is provided on the electric insulator fixed to the movable blade electrode which is turnably connected to the sheath conduit or the fixed blade electrode, wherein the coaxial cable is slid with respect to the sheath conduit so that parallel moving added to the coaxial cable is transmitted to the movable blade electrode as turnable moving about the pivot point via the force application point of the movable blade electrode to open and close the movable blade electrode and the fixed blade electrode, and wherein a high frequency wave can be applied between the movable blade electrode and the fixed blade electrode via the external electric conductor and the center electric conductor of the coaxial cable.

2. The endoscopic forceps according to claim 1, wherein the diameter of the cross section of the sheath conduit perpendicular to the center axis thereof is 2 mm to 4 mm.

3. The endoscopic forceps according to claim 1, wherein the high frequency wave is a microwave.

4. An endoscopic forceps apparatus comprising:
the endoscopic forceps according to claim 1; and
a high frequency wave transmitter.

\* \* \* \* \*